US011317784B2

(12) United States Patent
Takada et al.

(10) Patent No.: US 11,317,784 B2
(45) Date of Patent: May 3, 2022

(54) ENDOSCOPE

(71) Applicant: OLYMPUS CORPORATION, Tokyo (JP)

(72) Inventors: Keisuke Takada, Kokubunji (JP); Hiromasa Okano, Tachikawa (JP); Kazuki Honda, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 108 days.

(21) Appl. No.: 16/788,358

(22) Filed: Feb. 12, 2020

(65) Prior Publication Data

US 2020/0178768 A1 Jun. 11, 2020

Related U.S. Application Data

(63) Continuation of application No. PCT/JP2018/029669, filed on Aug. 7, 2018.

(30) Foreign Application Priority Data

Aug. 23, 2017 (JP) .............................. JP2017-160001

(51) Int. Cl.
*A61B 1/00* (2006.01)
*A61B 1/06* (2006.01)
*A61B 1/12* (2006.01)

(52) U.S. Cl.
CPC ...... *A61B 1/00096* (2013.01); *A61B 1/00091* (2013.01); *A61B 1/00181* (2013.01); *A61B 1/0661* (2013.01); *A61B 1/125* (2013.01)

(58) Field of Classification Search
CPC ..... A61B 1/12; A61B 1/00096; A61B 1/0661; A61B 1/00091; A61B 1/00;

(Continued)

(56) References Cited

U.S. PATENT DOCUMENTS

2011/0275889 A1* 11/2011 Kase .................. A61B 1/00177
600/103
2011/0282148 A1 11/2011 Kase et al.
(Continued)

FOREIGN PATENT DOCUMENTS

EP 2420178 A1 2/2012
EP 2649923 A1 10/2013
(Continued)

OTHER PUBLICATIONS

International Search Report dated Oct. 23, 2018 issued in PCT/JP2018/029669.

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscope includes an insertion portion; a first projecting portion; a second projecting portion; an illumination window disposed on an outer peripheral surface side of the first projecting portion, the illumination window being disposed about an axis along a longitudinal axis direction of the insertion portion, the illumination window having a light emitting surface from which an illumination light for illuminating an inside of a subject is emitted in a direction which includes a sideward direction of the insertion portion; and a mask configured to restrict sideward emission of the illumination light from the illumination window, wherein the mask has a shape inclined with respect to the longitudinal axis direction so as to increase a quantity of the illumination light emitted toward the second projecting portion from a distal end side toward a proximal end side of a distal end portion of the insertion portion.

20 Claims, 11 Drawing Sheets

(58) Field of Classification Search
CPC ... A61B 1/00181; A61B 1/125; A61B 1/0607;
A61B 1/126; A61B 1/0615; A61B
1/00177; G02B 23/26; G02B 23/2461
USPC .......................................... 600/109, 113, 157
See application file for complete search history.

(56) References Cited

U.S. PATENT DOCUMENTS

| | | | |
|---|---|---|---|
| 2011/0282155 A1* | 11/2011 | Kase | A61B 1/0615 600/165 |
| 2012/0157773 A1* | 6/2012 | Honda | A61B 1/00096 600/164 |
| 2013/0070072 A1* | 3/2013 | Honda | A61B 1/00163 348/76 |
| 2013/0137923 A1 | 5/2013 | Honda et al. | |
| 2014/0347878 A1* | 11/2014 | Honda | A61B 1/00177 362/574 |
| 2015/0073218 A1 | 3/2015 | Ito | |
| 2018/0092515 A1* | 4/2018 | Yashiro | A61B 1/00045 |

FOREIGN PATENT DOCUMENTS

| | | |
|---|---|---|
| EP | 2901913 A1 | 8/2015 |
| JP | 2012-157577 A | 8/2012 |
| WO | WO 2011/055641 A1 | 5/2011 |
| WO | WO 2012/137737 A1 | 10/2012 |
| WO | WO 2014/050236 A1 | 4/2014 |

\* cited by examiner

ENDOSCOPE

CROSS REFERENCE TO RELATED APPLICATION

This application is a continuation application of PCT/JP2018/029669 filed on Aug. 7, 2018 and claims benefit of Japanese Application No. 2017-160001 filed in Japan on Aug. 23, 2017, the entire contents of which are incorporated herein by this reference.

BACKGROUND OF THE INVENTION

1. Field of the Invention

The present invention relates to an endoscope, and more particularly to an endoscope capable of observing an inside of a subject with a wide-angle field of view.

2. Description of the Related Art

In a medical field, to prevent a failure of finding a lesion part or the like, there has been recently proposed an endoscope capable of observing an inside of a subject with a wide-angle field of view. As one example of such an endoscope, there has been known an endoscope which has fields of view in front of and on a side of an elongated insertion portion configured to be inserted into the subject.

More specifically, for example, International Publication No. WO2014/050236 discloses a configuration where a lens unit having a front-view type observation window on which an optical image of an object to be observed in an inserting direction which is an axial direction of an insertion portion of an endoscope is incident and a side-view type observation window on which an optical image of an object to be observed on a side in the axial direction is incident, a pedestal which projects so as to have the same surface height as the front-view type observation window at a position where the pedestal is disposed adjacently to the lens unit, and a cylindrical lens frame which supports respective lenses of the lens unit are disposed on a distal end portion of the insertion portion. International Publication No. WO2014/050236 also discloses a configuration where at least a part of the lens frame is formed of a light guide member which guides an illumination light, and the illumination light is radiated to a field of view of observation of the side-view type observation window from the lens frame.

According to the configuration disclosed in International Publication No. WO2014/050236, for example, at the time of near view observation where observation is performed by moving the distal end portion of the insertion portion close to the object to be observed, it is possible to obtain an image where a light and dark contrast is conspicuously high between a region where an illumination light is radiated to the object to be observed and a region where a shade is formed due to interruption of the illumination light by the pedestal.

SUMMARY OF THE INVENTION

An endoscope according to one aspect of the present invention includes: an insertion portion configured to be inserted into a subject; a first projecting portion disposed on a distal end portion of the insertion portion in a projecting manner along a longitudinal axis direction of the insertion portion; a second projecting portion disposed on the distal end portion of the insertion portion at a position adjacently to the first projecting portion, the second projecting portion being disposed in a projecting manner along the longitudinal axis direction of the insertion portion; an illumination window disposed on an outer peripheral surface side of the first projecting portion, the illumination window being disposed about an axis along the longitudinal axis direction of the insertion portion, the illumination window having a light emitting surface from which an illumination light for illuminating an inside of the subject is emitted in a direction which includes a sideward direction of the insertion portion; and a mask configured to restrict sideward emission of the illumination light from the illumination window, wherein the mask has a shape inclined with respect to the longitudinal axis direction so as to increase a quantity of the illumination light emitted toward the second projecting portion from a distal end side toward a proximal end side of the distal end portion of the insertion portion.

DETAILED DESCRIPTION OF THE PREFERRED EMBODIMENTS

Hereinafter, embodiments of the present invention are described with reference to drawings.

First Embodiment

FIG. 1 to FIG. 11 relate to a first embodiment of the present invention.

Figure 1:
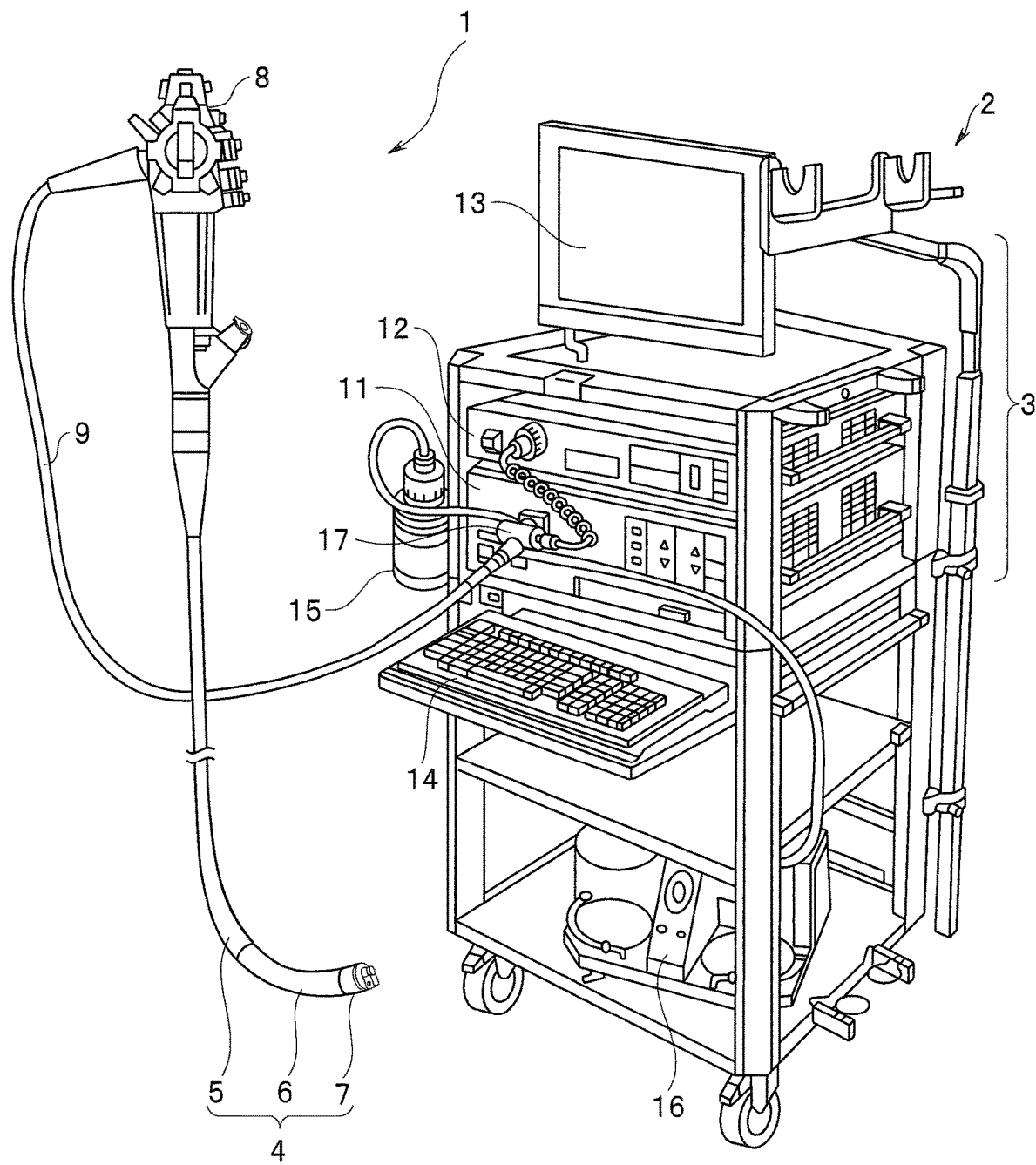
FIG. 1 is a view showing a configuration of a main part of an endoscope apparatus including an endoscope according to a first embodiment.

As shown in FIG. 1, an endoscope apparatus according to this embodiment includes an endoscope 1, and equipment 3 for endoscope mounted on a movable trolley 2. Note that, in the description made hereinafter, the description is made by taking a flexible endoscope as an example. However, this embodiment is also applicable to a rigid endoscope. FIG. 1 is a view showing a configuration of a main part of the endoscope apparatus including the endoscope according to the embodiment.

The endoscope 1 has an elongated insertion portion 4 which is inserted into a subject such as a living body. The insertion portion 4 has an elongated flexible tube 5 which is disposed on a proximal end side of the insertion portion 4, a bending portion 6 disposed on a distal end side of the flexible tube 5, and a distal end portion 7 disposed on a distal end side of the bending portion 6. The endoscope 1 also includes an operation portion 8 which has a bending operation knob for a bending operation of the bending portion 6 and a scope switch such as a release switch, and disposed on a proximal end side with respect to the insertion portion 4, and a universal cable 9 which extends from the operation portion 8.

The equipment 3 for endoscope includes: a light source device 11 configured to emit an illumination light for illuminating an object in the subject such as a living body tissue existing in a living body; a video processor 12 configured to generate a video signal by applying predetermined processing to a pickup image signal obtained at the time of picking up an image of the subject by the endoscope 1 and outputs the video signal; a monitor 13 configured to display an observation image corresponding to the video signal outputted from the video processor 12; and a keyboard 14 with which a command and data corresponding to an operation of a user can be input to the video processor 12.

On the other hand, a bottle 15 for storing cleaning liquid such as water or normal saline which is a liquid used for cleaning or the like is detachably mounted on a strut of the trolley 2. An air feeding pump unit (not shown in the drawing) is disposed in any one of devices of the equipment 3 for endoscope.

When air supplied from the air feeding pump unit flows into the bottle 15, a cleaning liquid is supplied to each cleaning nozzle disposed on the distal end portion 7 by way of an air/liquid feeding channel (not shown in the drawing) in the endoscope 1. A suction unit 16 which sucks a liquid and/or a gas ejected into the subject through the cleaning nozzle disposed on the distal end portion 7 is mounted on a shelf of the trolley 2.

The universal cable 9 is connected to the light source device 11 by a connector 17. In the endoscope 1 which includes the insertion portion 4 and the universal cable 9, a light guide LG (not shown in FIG. 1) which includes a plurality of optical fibers for transmitting an illumination light emitted from the light source device 11, a plurality of signal lines (not shown in the drawing) for transmitting a pickup image signal and the like, and the air/liquid feeding channel which is formed as flow paths for a gas and a liquid are disposed. The connector 17 connected to the universal cable 9 on the equipment 3 for endoscope side branches into the signal lines, a tube, and the light guide such that the signal lines, the tube, and the light guide are connected to the respective destinations.

In other words, the light guide LG is configured such that the light guide LG is disposed along a longitudinal axis direction of the insertion portion 4, and transmits the illumination light for illuminating the inside of a subject (an object existing in the subject) from the proximal end portion to the distal end portion of the insertion portion 4. Although not shown in the drawing, a distal end portion of the light guide LG is branched in two directions in a vicinity of the distal end portion 7 of the insertion portion 4.

Figure 2:
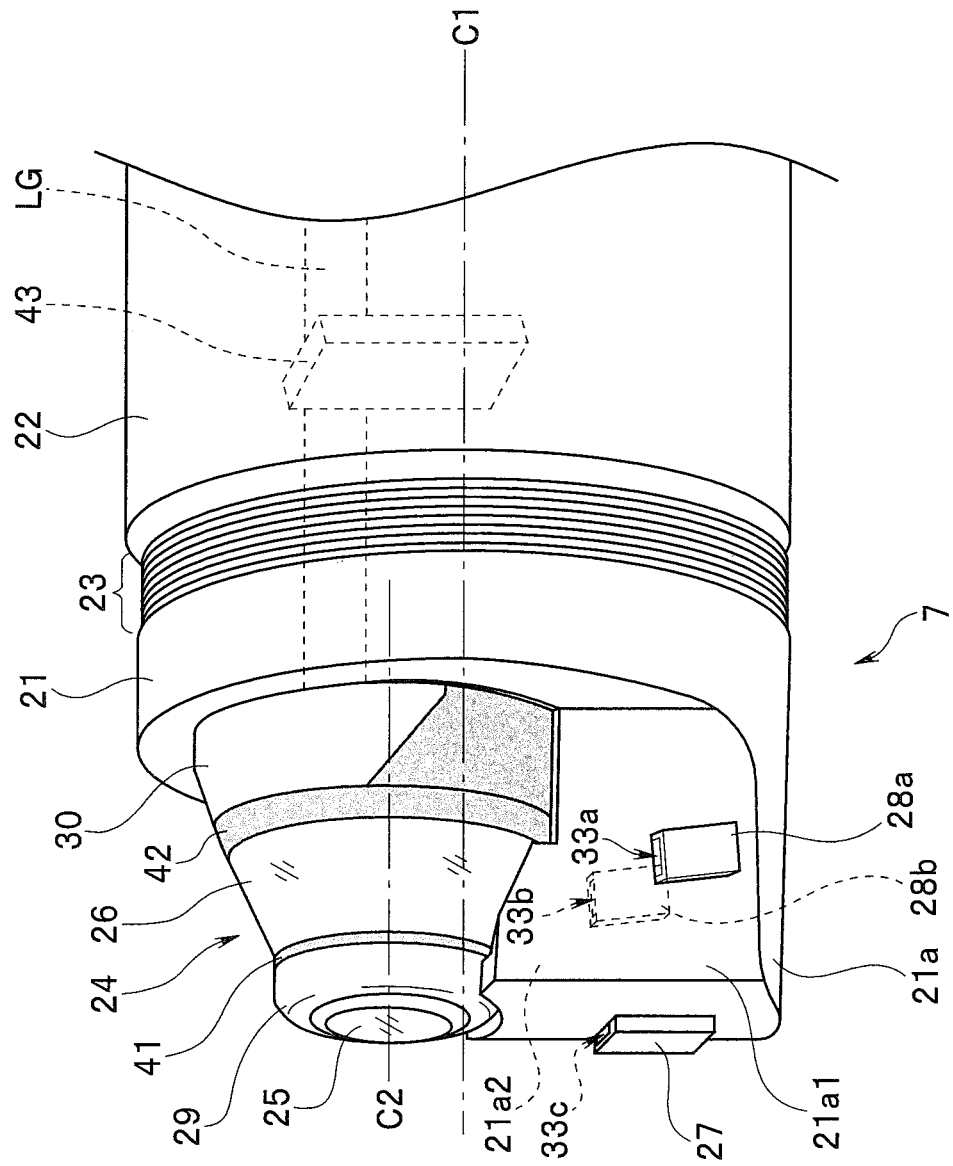
FIG. 2 is a perspective view showing one example of a configuration of a distal end portion of the endoscope according to the first embodiment.

As shown in FIG. 2, the distal end portion 7 of the insertion portion 4 includes a distal end portion body 21 made of a resin. The insertion portion 4 is covered by a sheath member 22 made of rubber. A distal end portion of the sheath member 22 is fixed to the distal end portion body 21 by a thread wound portion 23. An adhesive agent is applied to the thread wound portion 23. An image pickup device 43 is disposed in the distal end portion 7. The image pickup device 43 is configured such that incident light incident from a front observation window 25 (described later) and a side observation window 26 (described later) respectively are received by an image pickup surface, an image of the received incident light is picked up, and a pickup image signal is outputted. Note that, as an example of the image pickup device 43 disposed in the distal end portion 7, a CCD, a CMOS or the like is named. FIG. 2 is a perspective view showing one example of the configuration of the distal end portion of the endoscope according to the embodiment.

In this embodiment, the description is made by assuming that a vertical direction of the distal end portion 7 of the insertion portion 4 is set as a direction which agrees with a vertical direction of the image pickup surface of the image pickup device 43.

A lens unit 24 which forms a projecting portion projecting along the longitudinal axis direction of the insertion portion 4 (first projecting portion) is disposed on a distal end surface of the distal end portion body 21. A pedestal portion 21a having a rectangular parallelepiped shape which forms a projecting portion projecting along the longitudinal axis direction of the insertion portion 4 (second projecting portion) is disposed on the distal end surface of the distal end portion body 21 at a position adjacently to the lens unit 24.

The lens unit 24 is disposed above the pedestal portion 21a in the distal end portion 7 of the insertion portion 4 in FIG. 2. The lens unit 24 further includes the front observation window 25 through which a front side of the insertion portion 4 (distal end portion 7) is observed, and the side observation window 26 through which a side of the insertion portion 4 (distal end portion 7) is observed. The lens unit 24 includes a front illumination window 29 which emits an illumination light transmitted by the light guide LG incorporated in the endoscope 1 toward a front side of the insertion portion 4 (distal end portion 7), and a side illumination window 30 which diffuses the illumination light and emits the illumination light in directions including a sideward direction of the insertion portion 4 (distal end portion 7). An image pickup optical system (not shown in the drawing) is disposed in the lens unit 24. The image pickup optical system includes a plurality of lenses which faun images of incident light incident from the front observation window 25 and the side observation window 26 respectively on the image pickup surface of the image pickup device 43.

In other words, according to the above-mentioned configuration, an image of an object which exists in front of the insertion portion 4 (distal end portion 7) and an image of an object which exists on a side of the insertion portion 4 (distal end portion 7) can be simultaneously picked up by the image pickup device 43. Also according to the above-mentioned configuration, the monitor 13 displays an observation image having a wide-angle field of view which allows simultaneous observation of the object which exists in front of the insertion portion 4 (distal end portion 7) and the object which exists on a side of the insertion portion 4 (distal end portion 7) as an observation image corresponding to a pickup image signal outputted from the image pickup device 43.

Note that, "in front of the insertion portion 4 (distal end portion 7)" means a direction along a longitudinal axis C1 of the insertion portion 4 (see FIG. 2), for example. In this embodiment, "in front of the insertion portion 4" includes the direction along the longitudinal axis direction of the insertion portion 4. On the other hand, "on a side of the insertion portion 4 (distal end portion 7)" is a direction which intersects with the longitudinal axis C1 of the insertion portion 4 (see FIG. 2), for example. In this embodiment, "on a side of the insertion portion 4" includes the direction which intersects in the longitudinal axis direction of the insertion portion 4. As the direction which intersects in the longitudinal axis direction of the insertion portion 4, an orthogonal direction is named, for example.

The front observation window 25 is formed of a circular lens, for example, and is disposed on a distal end surface of the lens unit 24. The front observation window 25 has an optical axis which passes a center of the side observation window 26 and is parallel to the longitudinal axis direction of the insertion portion 4. In other words, the front observation window 25 has the optical axis which agrees with a center axis C2 of the lens unit 24 (see FIG. 2) which is an axis parallel to the longitudinal axis direction of the insertion portion 4. The front observation window 25 has a field of view in front of the insertion portion 4 (distal end portion 7).

The side observation window 26 is disposed on a proximal end side of the front illumination window 29, that is, is disposed between the front observation window 25 and the side illumination window 30 about the center axis C2 of the lens unit 24. The side observation window 26 has a field of view on a side of the insertion portion 4 (distal end portion 7). Note that the side observation window 26 may preferably be formed of a frustoconical lens which includes a tapered surface gradually decreasing its diameter from a proximal end side toward a distal end side of the lens unit 24 as an outer peripheral surface.

The pedestal portion 21a is disposed at a position adjacently to the lens unit 24, and is formed as a distal end structural body having a distal end surface disposed substantially at the same height (a projecting height toward a front side) as a surface of the front observation window 25. A cleaning nozzle 27 which cleans the surface of the front observation window 25 is disposed on the distal end surface of the pedestal portion 21a in a vicinity of the front observation window 25. Two cleaning nozzles 28a, 28b which clean a surface of the side observation window 26 are disposed on two side surfaces 21a1, 21a2 of the pedestal portion 21a disposed parallel to each other.

The cleaning nozzle 27 has an opening portion 33c which is configured such that a liquid is ejected from the opening portion 33c in a direction parallel to the distal end surface of the pedestal portion 21a, and the ejected liquid impinges on the surface of the front observation window 25. In other words, the cleaning nozzle 27 is configured to eject a liquid for cleaning the surface of the front observation window 25.

The cleaning nozzle 28a is disposed on the side surface 21a1 in a projecting manner. The cleaning nozzle 28a has an opening portion 33a which is configured to eject a liquid in a direction parallel to the side surface 21a1 from one end side of the side observation window 26 having an arcuate shape disposed on an outer peripheral surface of the lens unit 24. In other words, the cleaning nozzle 28a is configured to eject a liquid for cleaning a surface of the side observation window 26.

The cleaning nozzle 28b is disposed on the side surface 21a2 in a projecting manner. The cleaning nozzle 28b has an opening portion 33b which is configured to eject a liquid in a direction parallel to the side surface 21a2 from the other end side of the side observation window 26 having an arcuate shape disposed on the outer peripheral surface of the lens unit 24. In other words, the cleaning nozzle 28b is configured to eject a liquid for cleaning the surface of the side observation window 26.

The front illumination window 29 is, for example, formed in an annular shape, and is positioned on a distal end portion of the lens unit 24 such that the front illumination window 29 surrounds a periphery of the front observation window 25. The front illumination window 29 is formed to have a light guide member and a diffusion/reflection member, for example. The front illumination window 29 is configured such that an illumination light emitted through a distal end portion (not shown in the drawing) of the light guide LG which is branched to an inside of the pedestal portion 21a is emitted to a front side of the insertion portion 4 (distal end portion 7). Further, a light blocking member 41 which prevents an illumination light emitted from the front illumination window 29 from being incident on the side observation window 26 is disposed in a region between the front illumination window 29 and the side observation window 26.

The side illumination window 30 is disposed on a proximal end side of the side observation window 26. The side illumination window 30 is formed to have a light guide member and a diffusion/reflection member, for example. The side illumination window 30 is also formed to have a light emitting surface which diffuses an illumination light emitted from the distal end portion (not shown in the drawing) of the light guide LG branched to the inside of the housing 31 (described later), and emits the illumination light in a direction including a side of the insertion portion 4 (distal end portion 7). Further, a light blocking member 42 which prevents an illumination light emitted from the side illumination window 30 from being incident on other portions of the lens unit 24 such as the side observation window 26 is disposed in a region between the side observation window 26 and the side illumination window 30.

Figure 3:
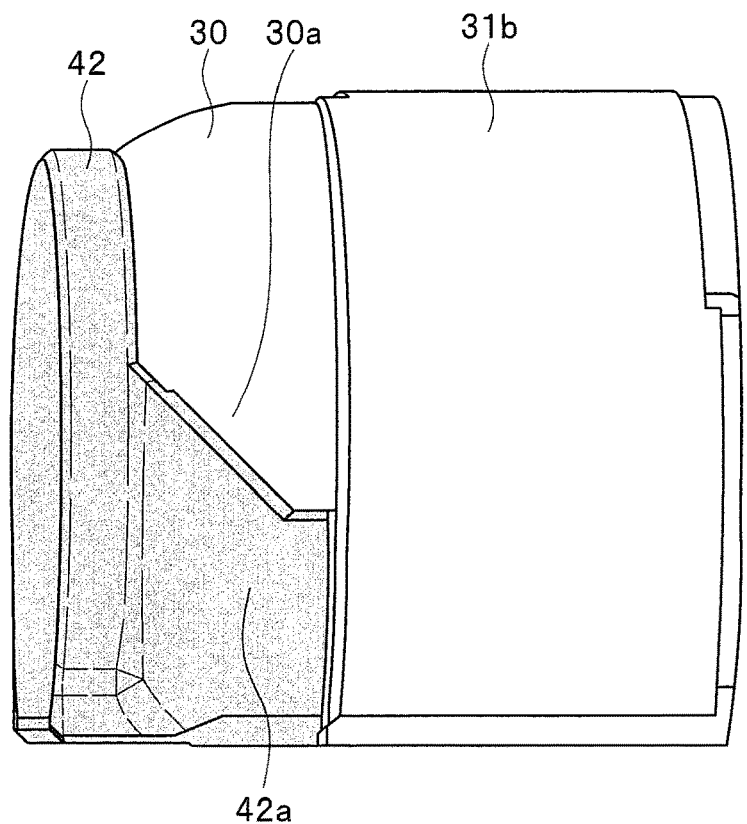
FIG. 3 is a side view for describing a specific example of a configuration of a side illumination window and portions around the side illumination window which are disposed on the distal end portion of the endoscope according to the first embodiment.
Figure 4:
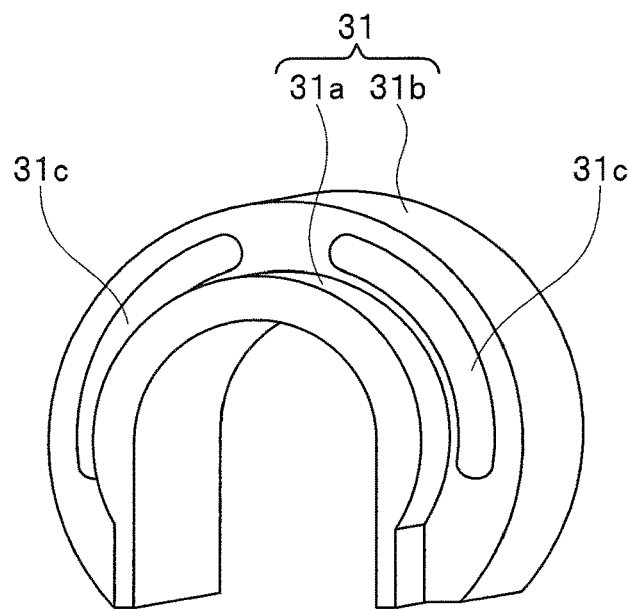
FIG. 4 is a perspective view for describing a specific example of a configuration of a housing disposed on the distal end portion of the endoscope according to the first embodiment.
Figure 5:
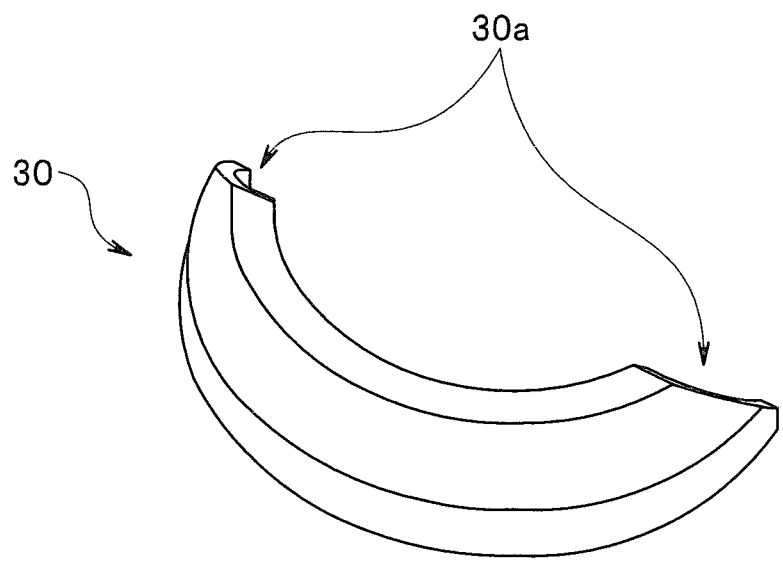
FIG. 5 is a perspective view for describing a specific example of a configuration of the side illumination window disposed on the distal end portion of the endoscope according to the first embodiment.
Figure 6:
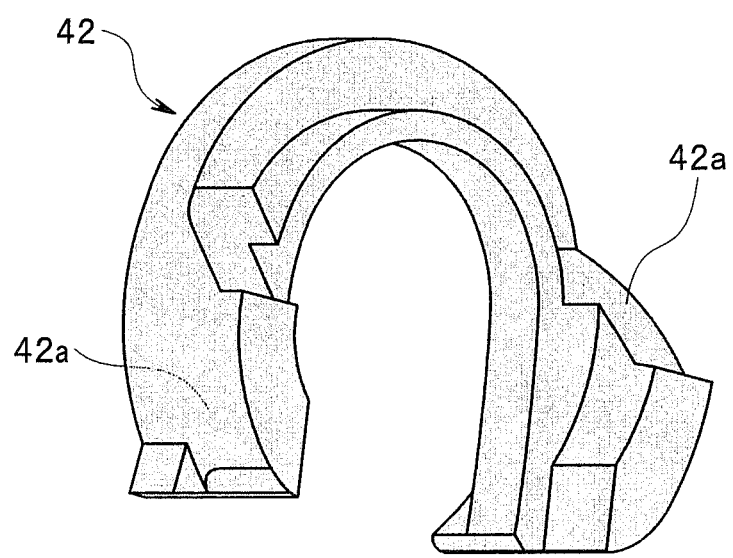
FIG. 6 is a perspective view for describing a specific example of a configuration of a light blocking member disposed on the distal end portion of the endoscope according to the first embodiment.

The specific configuration of the side illumination window 30 and portions around the side illumination window 30 is described with reference to FIG. 3 to FIG. 6. FIG. 3 is a side view for describing a specific example of a configuration of the side illumination window and portions around the side illumination window which are disposed on the distal end portion of the endoscope according to the first embodiment. FIG. 4 is a perspective view for describing a specific example of a configuration of the housing disposed on the distal end portion of the endoscope according to the first embodiment. FIG. 5 is a perspective view for describing a specific example of a configuration of the side illumination window disposed on the distal end portion of the endoscope according to the first embodiment. FIG. 6 is a perspective view for describing a specific example of a configuration of the light blocking member disposed on the distal end portion of the endoscope according to the first embodiment.

As shown in FIG. 3 and FIG. 4, for example, the housing 31 is configured such that a mounting portion 31a is formed on a distal end side of the housing 31. The mounting portion 31a is formed in a shape which allows mounting of the side illumination window 30 and the light blocking member 42 on the housing 31. The housing 31 is also configured such that a housing body 31b is formed on a proximal end side of the housing 31. The housing body 31b is disposed in the distal end portion body 21.

As shown in FIG. 4, for example, insertion holes 31c are formed in the housing body 31b. The insertion holes 31c are holes which allows the insertion and arrangement of distal end portions of the light guide LG in the insertion holes 31c in a direction parallel to the longitudinal axis direction of the insertion portion 4, and allows light emitting surfaces of the light guide LG to be disposed at positions which oppositely face a light incident surface of the side illumination window 30 mounted on the mounting portion 31a.

In other words, according to the above-mentioned configuration, an illumination light emitted through light emitting surfaces of the distal end portions of the light guide LG which is inserted and arranged in the insertion holes 31c is incident from the light incident surface of the side illumination window 30 mounted on the mounting portion 31a.

As shown in FIG. 5, for example, the side illumination window 30 is formed to have a light emitting surface having an arcuate shape. The side illumination window 30 is formed in a shape which allows mounting of the side illumination window 30 on an upper portion of the mounting portion 31a. The side illumination window 30 is configured to be arranged within a predetermined angle range corresponding to a range of approximately 180 degrees about the center axis C2 of the lens unit 24 when the side illumination window 30 is mounted on the upper portion of the mounting portion 31a. In other words, the side illumination window 30 is disposed about an axis along the longitudinal axis C1 of the insertion portion 4 on an outer peripheral surface side of the lens unit 24 and a proximal end side of the side observation window 26. More specifically, the side illumination window 30 is disposed about the center axis C2 of the lens unit 24 on the outer peripheral surface side of the lens unit 24 and the proximal end side of the side observation window 26. In this embodiment, in consideration of a layout or the like of the distal end portion 7, a center axis of the side illumination window 30 may not strictly agree with the center axis C2 of the lens unit 24.

As shown in FIG. 3 and FIG. 5, for example, end portions 30a of the side illumination window 30 are formed in an inclined shape such that a length of the side illumination window 30 in a circumferential direction is increased from a distal end side toward a proximal end side of the lens unit 24. More specifically, the end portions 30a are formed in an inclined shape which is inclined in a straight line shape at a predetermined angle with respect to a direction orthogonal to the circumferential direction of the side illumination window 30 on the light emitting surface (outer peripheral surface) of the side illumination window 30 having an arcuate shape. In this embodiment, it is assumed that the above-mentioned predetermined angle be set to 45 degrees or approximately 45 degrees, for example.

In other words, according to the above-mentioned configuration, the end portions of the light emitting surface of the side illumination window 30 are formed in a shape such that a quantity of an illumination light emitted toward a pedestal portion 21a side is increased from a distal end side toward a proximal end side of the distal end portion 7. Further, according to the above-mentioned configuration, both end portions of the light emitting surface of the side illumination window 30 having an arcuate shape are formed in an inclined shape such that the length of the side illumination window 30 in the circumferential direction is increased from the distal end side toward the proximal end side of the lens unit 24.

As shown in FIG. 6, for example, the light blocking member 42 is formed in an approximately inverse U shape. As shown in FIG. 3 and FIG. 6, for example, mask portions 42a are formed on a proximal end side of the light blocking member 42. The mask portions 42a are formed in a shape which allows mounting of the mask portions 42a on lower portions of the mounting portion 31a and in a shape which conforms with the inclined shape of the end portions 30a of the side illumination window 30 (a shape which allows the mask portions 42a to be brought into contact with the end portions 30a).

Figure 7:
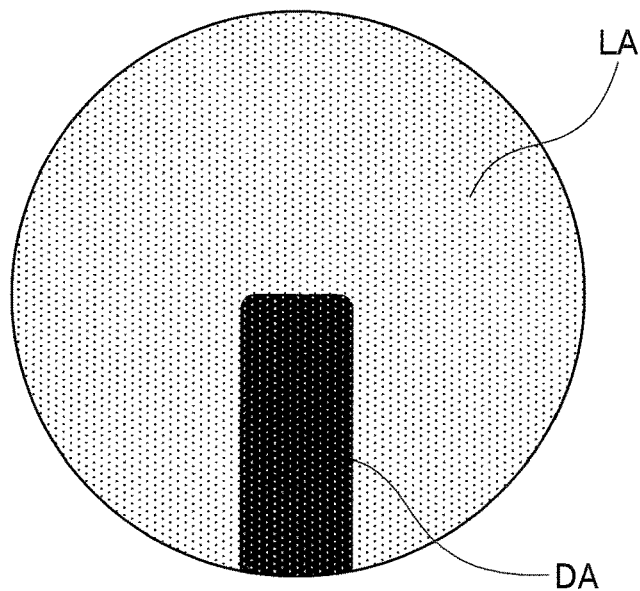
FIG. 7 is a schematic view for describing one example of an image obtained by a conventional endoscope having fields of view in front of and on a side of an insertion portion.

For example, International Publication No. WO2014/050236 discloses the configuration of a conventional endoscope having fields of view in front of and on a side of an elongated insertion portion configured to be inserted into a subject. With such a configuration, an image schematically shown in FIG. 7 can be obtained at the time of near view observation as an image where a light and dark contrast is conspicuously high between an illuminated region LA which is a region where an illumination light is radiated to an object to be observed and a shade region DA which is a region where a shade is formed due to interruption of the illumination light by a structural body projecting from a distal end portion of the insertion portion. Accordingly, with the configuration of the conventional endoscope having fields of view in front of and on a side of the elongated insertion portion configured to be inserted into the subject, at the time of near view observation where the observation is performed by making the distal end portion of the insertion portion approach the object existing in the subject, there is a possibility that the shade region DA which extends from a lower portion toward a center portion of an image obtained by the endoscope becomes conspicuous unintentionally. In such a case, there is a concern that a user who performs observation based on the image obtained by the endoscope having the above-mentioned fields of view feels a discomfort. FIG. 7 is a schematic view for describing one example of an image obtained by the conventional endoscope having fields of view in front of and on a side of the insertion portion.

Figure 8:
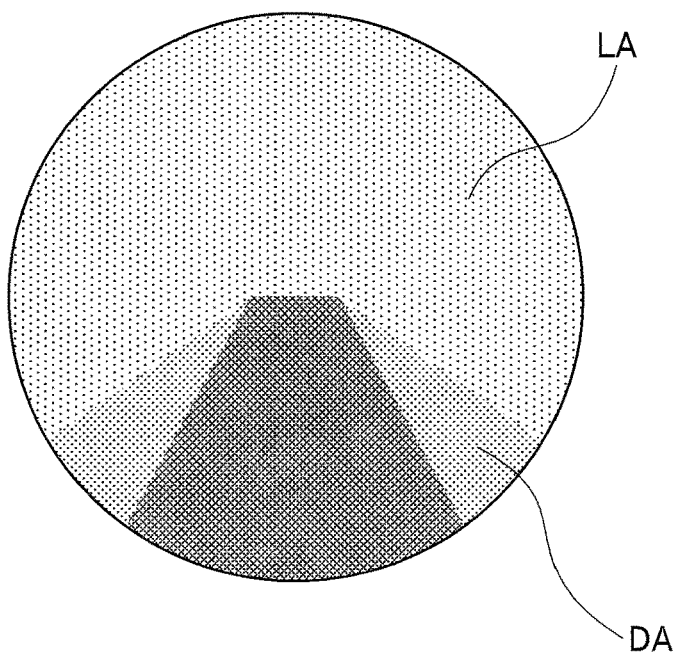
FIG. 8 is a schematic view for describing one example of an image obtained by the endoscope according to the first embodiment.

To the contrary, according to the configuration of the endoscope of this embodiment, the end portions 30a of the side illumination window 30 are formed in an inclined shape as described previously. Accordingly, an illumination light emitted from the side illumination window 30 toward the pedestal portion 21a side (a side below a center axis of the lens unit 24) can be gradually intensified from the distal end side toward the proximal end side of the distal end portion 7. Therefore, with the configuration according to this embodiment, it is possible to obtain an image schematically shown in FIG. 8 at the time of near view observation as an image where a light and dark contrast is suppressed between the illuminated region LA and the shade region DA. In this manner, according to this embodiment, it is possible to reduce a visual discomfort which a user may feel at the time of performing observation based on an image obtained in a state where illumination irregularities occur in a field of view of observation including fields of view in front of and on a side of the insertion portion. FIG. 8 is a schematic view for describing one example of an image obtained by the endoscope according to the embodiment.

According to this embodiment, provided that the end portions of the light emitting surface of the side illumination window 30 having an arcuate shape has an inclined shape where the length of the side illumination window 30 in the circumferential direction is increased from the distal end side toward the proximal end side of the lens unit 24, the end portions 30a may have a shape different from the shape illustrated in FIG. 3 and FIG. 5.

Figure 9:
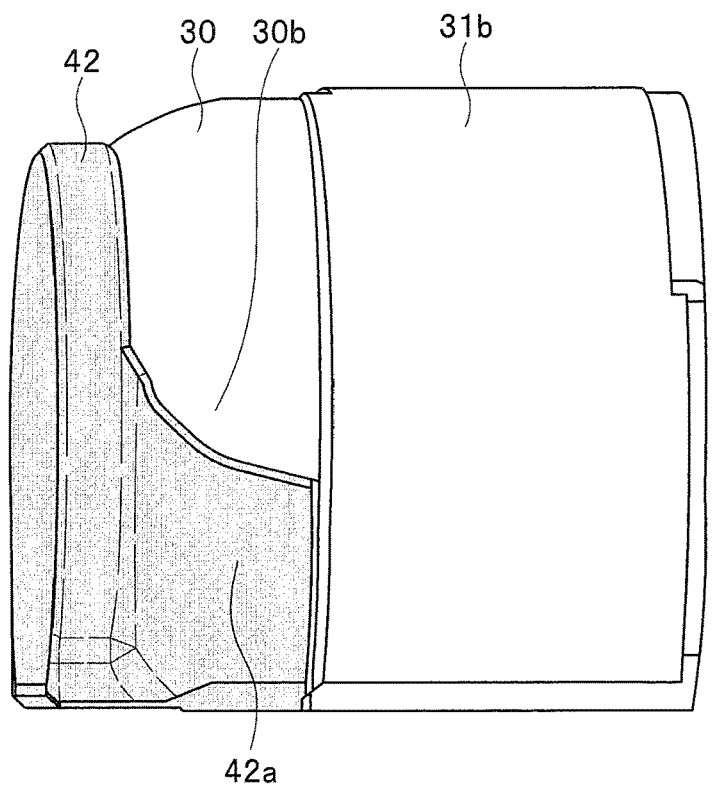
FIG. 9 is a side view for describing an example which differs from the example shown in FIG. 5 with respect to the configuration of the side illumination window disposed on the distal end portion of the endoscope according to the first embodiment.
Figure 10:
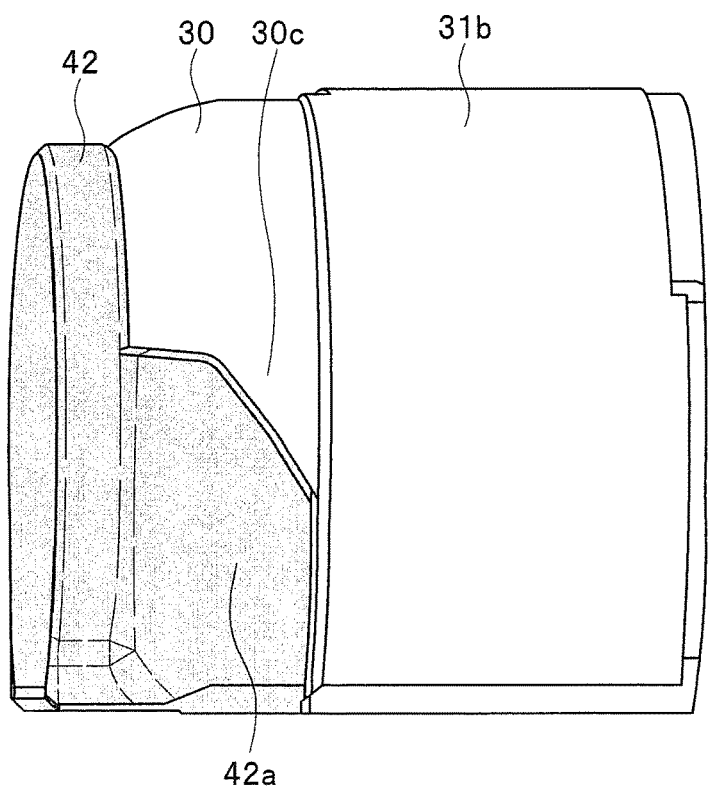
FIG. 10 is a side view for describing an example which differs from the example shown in FIG. 5 with respect to the configuration of the side illumination window disposed on the distal end portion of the endoscope according to the first embodiment.
Figure 11:
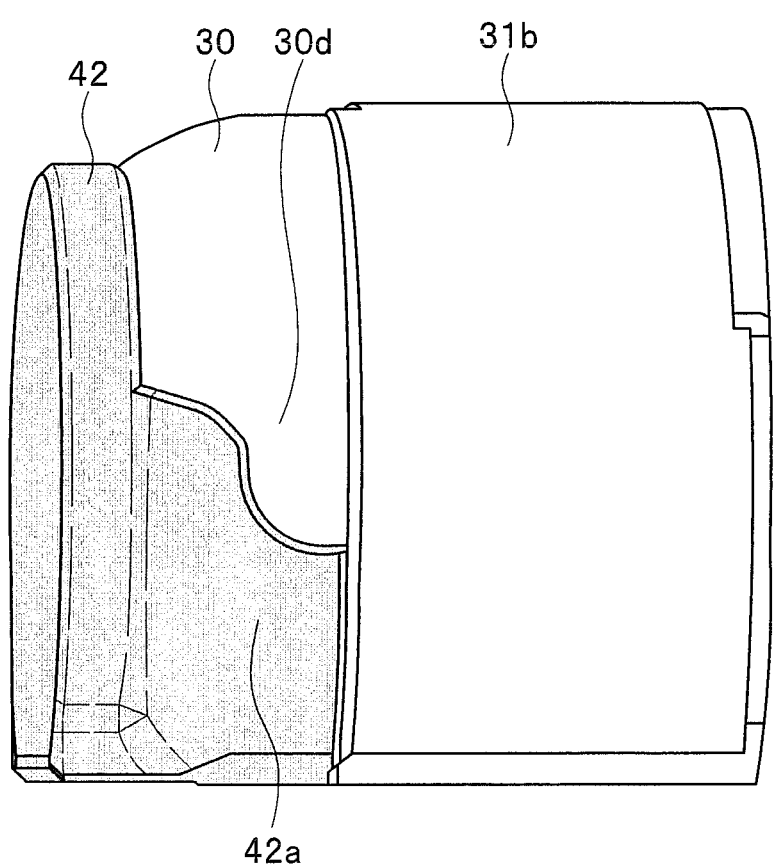
FIG. 11 is a side view for describing an example which differs from the example shown in FIG. 5 with respect to the configuration of the side illumination window disposed on the distal end portion of the endoscope according to the first embodiment.

More specifically, according to this embodiment, at least a portion of the end portion of the light emitting surface of the side illumination window 30 having an arcuate shape may have an inclined shape which is inclined in a curved manner with respect to a direction orthogonal to the circumferential direction of the side illumination window 30 on the light emitting surface (outer peripheral surface) such as the end portion 30b shown in FIG. 9, the end portion 30c shown in FIG. 10, and the end portion 30d shown in FIG. 11. FIG. 9, FIG. 10, and FIG. 11 are side views for describing examples which differ from the example shown in FIG. 5 with respect to the configuration of the side illumination window disposed on the distal end portion of the endoscope according to the first embodiment.

In this embodiment, the end portion of the light emitting surface of the side illumination window 30 having an arcuate shape may have an inclined shape which is inclined in a stepped manner with respect to a direction orthogonal to the circumferential direction of the side illumination window 30 on the light emitting surface (outer peripheral surface) similar to the shape of the end portion 30d shown in FIG. 11.

Second Embodiment

FIG. 12 to FIG. 17 relate to an endoscope according to a second embodiment of the present invention.

In this embodiment, the detailed description relating to components having substantially the same configurations as the corresponding components of the first embodiment is omitted, and the description is mainly performed relating to components having configurations different from the corresponding components of the first embodiment.

Figure 12:
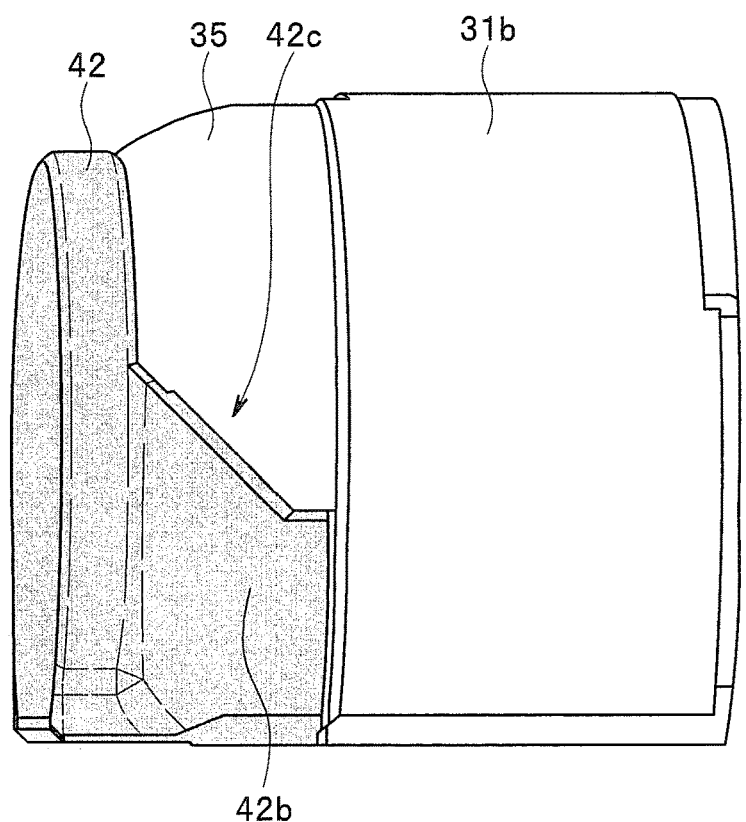
FIG. 12 is a side view for describing a specific example of a configuration of a side illumination window and portions around the side illumination window disposed on a distal end portion of an endoscope according to a second embodiment.
Figure 13:
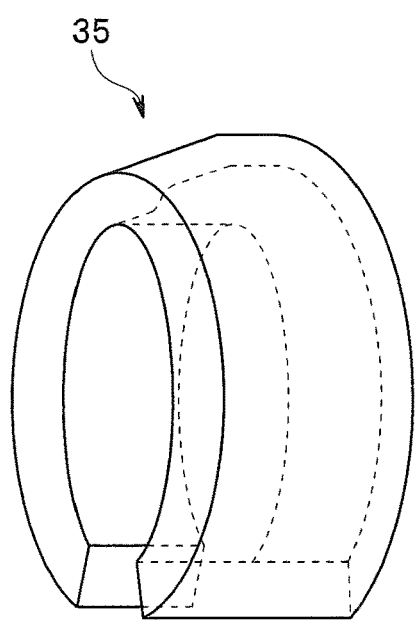
FIG. 13 is a view for describing a specific example of a configuration of the side illumination window disposed on the distal end portion of the endoscope according to the second embodiment.

In this embodiment, in place of the side illumination window 30, a side illumination window 35 shown in FIG. 12 and FIG. 13 is disposed on a proximal end side of the side observation window 26, for example. Further, in this embodiment, in place of the mask portions 42a, for example, mask portions 42b shown in FIG. 12 are formed on a proximal end side of the light blocking member 42. In other words, the mask portions 42b are integrally formed with the light blocking member 42 which prevents an illumination light emitted from the side illumination window 35 from being incident on the side observation window 26. FIG. 12 is a side view for describing a specific example of a configuration of the side illumination window and portions around the side illumination window disposed on a distal end portion of the endoscope according to the second embodiment. FIG. 13 is a view for describing a specific example of a configuration of the side illumination window disposed on the distal end portion of the endoscope according to the second embodiment.

As shown in FIG. 13, the side illumination window 35 is formed to have a light emitting surface having a partially annular shape, for example. The side illumination window 35 is also formed in a shape which allows mounting of the side illumination window 35 on the mounting portion 31a shown in FIG. 4. The side illumination window 35 is configured to be arranged within a range which exceeds 180 degrees about the center axis C2 of the lens unit 24 when the side illumination window 35 is mounted on an upper portion of the mounting portion 31a. In other words, the side illumination window 35 is mounted on the mounting portion 31a about an axis along the longitudinal axis C1 of the insertion portion 4 on a proximal end side of the side observation window 26. More specifically, the side illumination window 35 is disposed about the center axis C2 of the lens unit 24 on the proximal end side of the side observation window 26.

Figure 14:
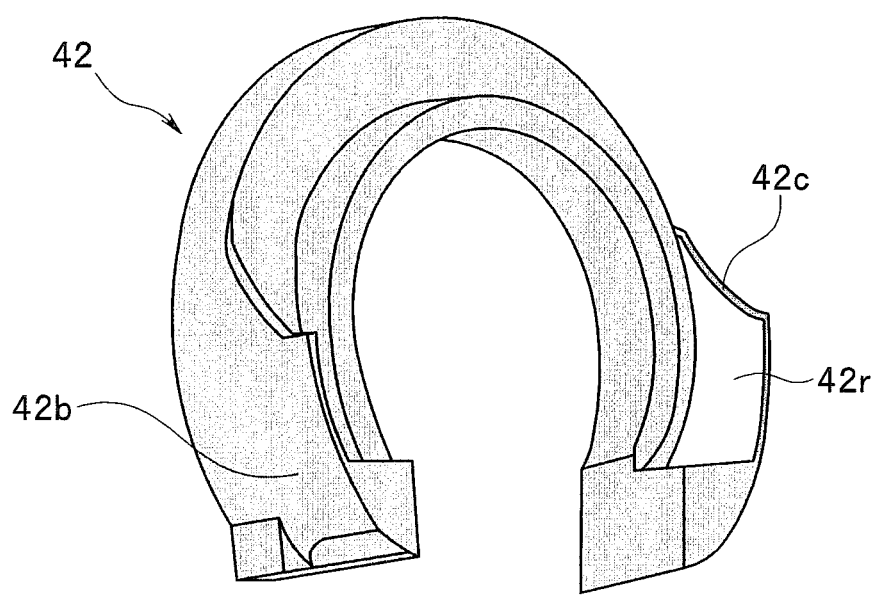
FIG. 14 is a perspective view for describing a specific example of a configuration of a light blocking member disposed on the distal end portion of the endoscope according to the second embodiment.

The mask portions 42b are formed in a shape which allows mounting of the mask portions 42b on lower portions of the mounting portion 31a. As shown in FIG. 12, the mask portions 42b are configured such that when the mask portions 42b are mounted on the lower portions of the mounting portion 31a, with respect to the light emitting surface (outer peripheral surface) of the side illumination window 35 having a partially annular shape, a surface of the light emitting surface which falls within a predetermined angle range corresponding to a range of approximately 180 degrees about the center axis C2 of the lens unit 24 is exposed to an outside as an exposed surface, and the mask portions 42b shield a surface of the light emitting surface which are disposed outside the predetermined angle range. As shown in FIG. 14, reflection members 42r are formed on a back surface side of the mask portions 42b. The reflection members 42r reflect an illumination light emitted from the light emitting surface (outer peripheral surface) of the side illumination window 35 and allow the reflected illumination light to be incident on the side illumination window 35 again. FIG. 14 is a perspective view for describing a specific example of a configuration of the light blocking member disposed on the distal end portion of the endoscope according to the second embodiment.

As shown in FIG. 12, inclined portions 42c are formed on the mask portions 42b. The inclined portions 42c are formed in an inclined shape such that a length of the above-mentioned exposed surface in the circumferential direction between both end portions is increased from the distal end side toward the proximal end side of the lens unit 24. More specifically, the inclined portions 42c are formed in an inclined shape where the inclined portions 42c are inclined in a straight line shape at a predetermined angle with respect to a direction orthogonal to the circumferential direction of the side illumination window 35 on the light emitting surface (outer peripheral surface) of the side illumination window 35 having a partially annular shape. In this embodiment, it is assumed that the above-mentioned predetermined angle be set to 45 degrees or approximately 45 degrees, for example.

In other words, according to the configuration described above, the end portions of the light emitting surface which falls within the exposed surface of the side illumination window 35 are formed in a shape such that a quantity of an illumination light emitted toward the pedestal portion 21a side is increased from the distal end side toward the proximal end side of the distal end portion 7.

As has been described above, according to the configuration of the endoscope of this embodiment, the inclined portions 42c of the mask portions 42b are formed in an inclined shape as described above. Accordingly, a quantity of an illumination light emitted from the side illumination window 35 to the pedestal portion 21a side (a side below the center axis of the lens unit 24) can be gradually increased from the distal end side toward the proximal end side of the distal end portion 7. Therefore, with the configuration according to this embodiment, an image schematically shown in FIG. 8 can be obtained at the time of near view observation. As a result, according to this embodiment, it is possible to reduce a visual discomfort which a user may feel at the time of performing observation based on an image obtained in a state where illumination irregularities occur in a field of view of observation including fields of view in front of and on a side of the insertion portion.

According to this embodiment, the inclined portions 42c are not limited to be formed in the inclined shape described above, and may be formed in an inclined shape which is inclined in a curved manner or a stepped manner with respect to a direction orthogonal to the circumferential direction of the side illumination window 35 on the light emitting surface (outer peripheral surface) of the side illumination window 35 having a partially annular shape.

In this embodiment, the mask portions 42b are integrally formed with the light blocking member 42. However, this embodiment is not limited to such a configuration, and the mask portions 42b may be formed as separate bodies from the light blocking member 42.

In this embodiment, in place of forming the mask portions 42b on the light blocking member 42, for example, a black paint or the like may be applied to portions of the light emitting surface (outer peripheral surface) of the side illumination window 35 such that the painted portions have substantially the same shape as the mask portions 42b and the inclined portions 42c. A specific example of the configuration of an endoscope according to a modification of this embodiment is described hereinafter.

Figure 15:
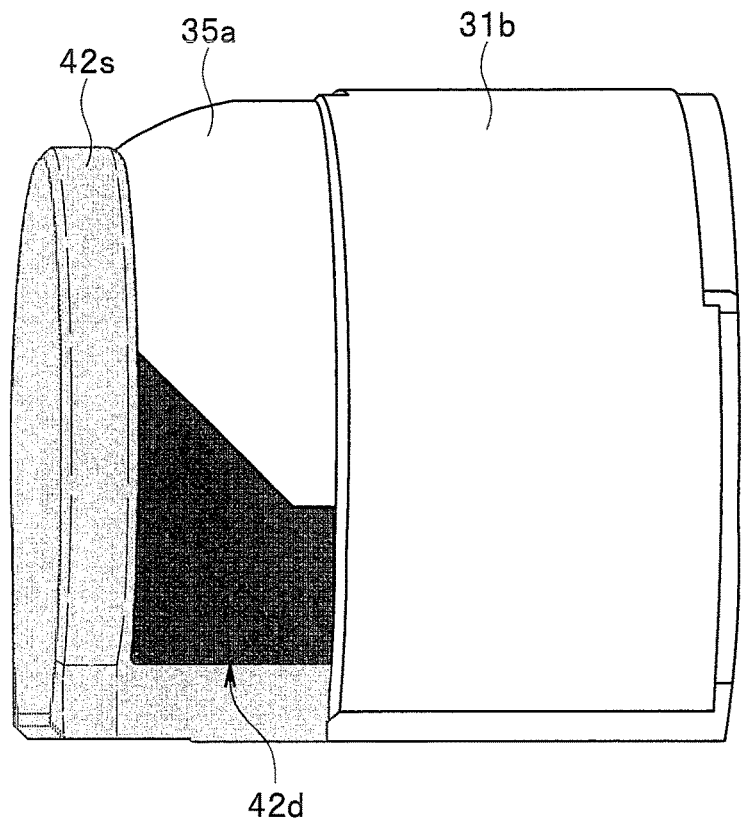
FIG. 15 is a side view for describing a specific example of a configuration of a side illumination window and portions around the side illumination window disposed on a distal end portion of an endoscope according to a modification of the second embodiment.
Figure 16:
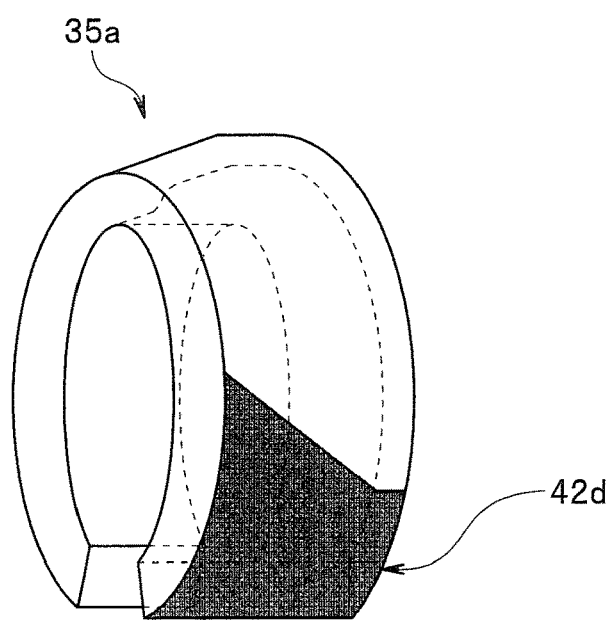
FIG. 16 is a view for describing the specific example of the configuration of the side illumination window disposed on the distal end portion of the endoscope according to the modification of the second embodiment.
Figure 17:
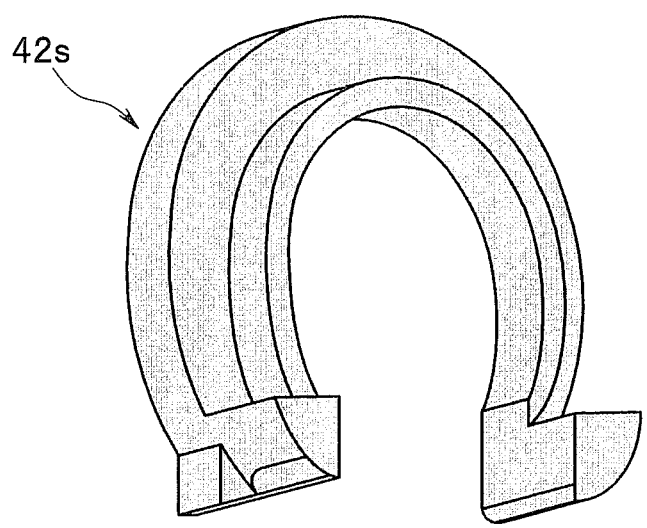
FIG. 17 is a perspective view for describing a specific example of a configuration of a light blocking member disposed on the distal end portion of the endoscope according to the modification of the second embodiment.

In this modification, in place of the side illumination window 35, for example, a side illumination window 35a shown in FIG. 15 and FIG. 16 may be disposed on the proximal end side of the side observation window 26. Further, in this modification, in place of the light blocking member 42, for example, a light blocking member 42s shown in FIG. 15 and FIG. 17 is mounted on a mounting portion 31a of a housing 31. FIG. 15 is a side view for describing the specific example of a configuration of the side illumination window and portions around the side illumination window disposed on a distal end portion of the endoscope according to the modification of the second embodiment. FIG. 16 is a view for describing the specific example of the configuration of the side illumination window disposed on the distal end portion of the endoscope according to the modification of the second embodiment. FIG. 17 is a perspective view for describing a specific example of a configuration of a light blocking member disposed on the distal end portion of the endoscope according to the modification of the second embodiment.

As shown in FIG. 16, for example, the side illumination window 35a is formed to have a light emitting surface having a partially annular shape. The side illumination window 35a is also formed in a shape which allows mounting of the side illumination window 35a on the mounting portion 31a shown in FIG. 4. The side illumination window 35a is configured to be arranged within a range which exceeds 180 degrees about the center axis C2 of the lens unit 24 when the side illumination window 35a is mounted on an upper portion of the mounting portion 31a. In other words, the side illumination window 35a is mounted on the mounting portion 31a about an axis along the longitudinal axis C1 of the insertion portion 4 on a proximal end side of the side observation window 26. More specifically, the side illumination window 35a is disposed about the center axis C2 of the lens unit 24 on the proximal end side of the side observation window 26.

Light blocking surfaces 42d which are regions in which a black (light blocking) paint is applied are formed on both end portions of the light emitting surface of the side illumination window 35a such that the light blocking surfaces 42d have an inclined shape similar to the inclined shape of the inclined portion 42c of the mask portion 42b, for example.

More specifically, as shown in FIG. 15 and FIG. 16, for example, the light blocking surfaces 42d are formed in such a way that a black (light blocking) paint is applied to surfaces of the light emitting surface (outer peripheral surface) of the side illumination window 35a having a partially annular shape. Such surfaces of the light emitting surface are disposed outside a predetermined angle range corresponding to a range of approximately 180 degrees about the center axis C2 of the lens unit 24. In other words, the light blocking surfaces 42d are configured such that the surface of the light emitting surface (outer peripheral surface) of the side illumination window 35a having a partially annular shape which falls within a predetermined angle range corresponding to a range of approximately 180 degrees about the center axis C2 of the lens unit 24 is exposed to an outside as an exposed surface, and the surfaces which are disposed outside the predetermined angle range are shielded. In other words, the light blocking surfaces 42d are formed by applying light blocking processing to the surfaces of the light emitting surface (outer peripheral surface) of the side illumination window 35a which are disposed outside the above-mentioned predetermined angle range.

The light blocking surfaces 42d are formed by applying a black (light blocking) paint so as to have an inclined shape where inclined shapes are inclined in a straight line shape at a predetermined angle with respect to a direction orthogonal to a circumferential direction of the side illumination window 35a on the light emitting surface (outer peripheral surface) of the side illumination window 35a having a partially annular shape. In other words, the light blocking surfaces 42d are formed to have the inclined shape such that a length of the above-mentioned exposed surface in the circumferential direction between both end portions is increased from the distal end side toward the proximal end side of the lens unit 24.

Provided that the light blocking surfaces 42d are formed by applying light blocking processing to the surfaces of the light emitting surface (outer peripheral surface) of the side illumination window 35a which are disposed outside the above-mentioned predetermined angle range, the light blocking surfaces 42d may be formed by applying processing other than applying a black (light blocking) paint. More specifically, for example, the light blocking surfaces 42d may be formed by applying a colored adhesive agent to the both end portions of the light emitting surface (outer peripheral surface) of the side illumination window 35a. The light blocking surfaces 42d may also be formed by wrapping the both end portions of the light emitting surface with a tacky sheet. The light blocking surfaces 42d may be also formed by applying surface processing such as plating to the both end portions of the light emitting surface.

As shown in FIG. 17, for example, a light blocking member 42s is formed in an approximately inverse U shape. The light blocking member 42s is disposed in a region between the side observation window 26 and the side illumination window 35a. The light blocking member 42s is configured to prevent an illumination light emitted from the side illumination window 35a from being incident on other portions of the lens unit 24 such as the side observation window 26. Proximal end sides of the light blocking member 42s are formed in a shape which conforms with a shape of the both end portions of the side illumination window 35a (a shape which allows the proximal end sides to be brought into contact with the both end portions of the side illumination window 35a). In other words, the light blocking member 42s does not have the structure which corresponds to the mask portions 42a and the mask portions 42b.

The configuration of the endoscope according to the modification described above also can obtain the image schematically shown in FIG. 8 at the time of near view observation. Accordingly, by adopting the configuration of the endoscope according to the modification, it is possible to reduce a visual discomfort which a user may feel at the time of performing observation based on an image obtained in a state where illumination irregularities occur in a field of view of observation including fields of view in front of and on a side of the insertion portion.

In this modification, for example, light reflecting surfaces (not shown in the drawing) which reflect an illumination light emitted from the light emitting surface (outer peripheral surface) of the side illumination window 35a and allow the reflected illumination light to be incident on the side illumination window 35a again may be formed in a layer form on portions sandwiched between the light emitting surface (outer peripheral surface) of the side illumination window 35a and the light blocking surfaces 42d. In such a configuration, for example, at both end portions of the light emitting surface (outer peripheral surface) of the side illumination window 35a, the light reflecting surfaces may be formed by applying a paint having high reflectivity so as to have an inclined shape as described above, and the light blocking surfaces 42d may be formed by applying a black (light blocking) paint in an overlapping manner to upper layers of the formed light reflecting surfaces.

The present invention is not limited to the above-mentioned respective embodiments, and various modifications and applications are conceivable without departing from the gist of the present invention.

What is claimed is:

1. An endoscope comprising:
   an insertion portion configured to be inserted into a subject;
   a first projecting portion disposed on a distal end portion of the insertion portion in a projecting manner along a longitudinal axis direction of the insertion portion;
   a second projecting portion disposed on the distal end portion of the insertion portion at a position adjacently to the first projecting portion, the second projecting portion being disposed in a projecting manner along the longitudinal axis direction of the insertion portion;
   an illumination window disposed on an outer peripheral surface side of the first projecting portion, the illumination window being disposed about an axis along the longitudinal axis direction of the insertion portion, the illumination window having a light emitting surface from which an illumination light for illuminating an inside of the subject is emitted in a direction which includes a sideward direction of the insertion portion; and
   a mask configured to restrict sideward emission of the illumination light from the illumination window, wherein
   the mask has a shape inclined with respect to the longitudinal axis direction so as to increase a quantity of the illumination light emitted toward the second projecting portion from a distal end side toward a proximal end side of the distal end portion of the insertion portion.

2. The endoscope according to claim 1, wherein the mask is formed to shield a portion of the illumination window.

3. The endoscope according to claim 1, wherein the light emitting surface having an arcuate shape such that the light emitting surface is disposed within a range of approximately 180 degrees about a center axis of the first projecting portion which is an axis along the longitudinal axis direction of the insertion portion, and
   both end portions of the light emitting surface having the arcuate shape are formed in an inclined shape such that a length of the illumination window in a circumferential direction is increased from a distal end side toward a proximal end side of the first projecting portion.

4. The endoscope according to claim 3, wherein the inclined shape is a shape inclined in one of a straight manner, a curved manner, or a stepped manner with respect to a direction orthogonal to the circumferential direction of the illumination window on the light emitting surface having the arcuate shape.

5. The endoscope according to claim 1, wherein the light emitting surface having a partially annular shape such that the light emitting surface is disposed within a range which exceeds 180 degrees about a center axis of the first projecting portion which is an axis along the longitudinal axis direction of the insertion portion,
   the mask is formed to expose a surface of the light emitting surface having the partially annular shape which falls within a predetermined angle range corresponding to a range of approximately 180 degrees about the center axis of the first projecting portion to an outside as an exposed surface, and shields at least a portion of a surface of the light emitting surface having the partially annular shape disposed outside the predetermined angle range, and
   an inclined shape of the mask forms an inclined portion by which a length of the exposed surface in a circumferential direction between both end portions of the exposed surface is increased from a distal end side toward a proximal end side of the first projecting portion.

6. The endoscope according to claim 5, wherein the inclined portion has a shape inclined in one of a straight manner, in a curved manner, or in a stepped manner with respect to a direction orthogonal to the circumferential direction of the illumination window on the light emitting surface having the partially annular shape.

7. The endoscope according to claim 5, further comprising:
a first observation window disposed on a distal end surface of the first projecting portion, the first observation window having a field of view in front of the insertion portion; and
a second observation window disposed between the first observation window and the illumination window about a center axis of the first projecting portion, the second observation window having a field of view on a side of the insertion portion, wherein
the mask is integrally formed with a light blocking member which prevents the illumination light emitted from the illumination window from being incident on the second observation window.

8. The endoscope according to claim 7, further comprising:
a first nozzle disposed on the second projecting portion and configured to eject a liquid for cleaning a surface of the first observation window; and
a second nozzle disposed on the second projecting portion and configured to eject a liquid for cleaning a surface of the second observation window.

9. The endoscope according to claim 7 further comprising an image pickup device configured to pick up an image by receiving incident light incident from the first observation window and the second observation window respectively on an image pickup surface, wherein
a vertical direction of the distal end portion of the insertion portion is set as a direction which agrees with a vertical direction of the image pickup surface, and
the first projecting portion is disposed above the second projecting portion at the distal end portion of the insertion portion.

10. The endoscope according to claim 5, wherein the mask comprises a light blocking material disposed on a surface of the light emitting surface having the partially annular shape outside the predetermined angle range.

11. The endoscope according to claim 1, further comprising:
a mounting portion formed in a shape which allows mounting of the illumination window on the mounting portion;
a light guide configured to transmit the illumination light from a proximal end portion to the distal end portion of the insertion portion; and
an insertion hole formed as a hole for arranging a light emitting surface of the light guide at a position which opposedly faces a light incident surface of the illumination window mounted on the mounting portion.

12. An endoscope comprising:
an insertion portion configured to be inserted into a subject;
a first projection projecting from a distal end of the insertion portion in a longitudinal axis direction, the first projection having an illumination window disposed on an outer peripheral surface of the first projection, the illumination window being disposed at least partially in a circumferential direction around the longitudinal axis direction so as to emit illumination light in the radial direction from a light emitting surface;
a second projection projecting from the distal end in the longitudinal axis direction at a position offset from the first projection in a radial direction; and
a mask configured to restrict emission of the illumination light in the radial direction from the illumination window, wherein the mask has a shape that increases in the radial direction from a proximal end side of the illumination window to a distal end side of the illumination window.

13. The endoscope according to claim 12, wherein the shape between the proximal end side and distal end side of the illumination window being one of linear, curved, stepped or any combination thereof.

14. The endoscope according to claim 12, wherein:
the mask being formed partially in the circumferential direction and having the shape on each of first and second ends;
the illumination window being formed partially in the circumferential direction to define third and fourth ends of the illumination window; and
the third and fourth ends of the illumination window having the shape so as to mate with the first and second ends of the mask.

15. The endoscope according to claim 12, wherein:
the mask being formed partially in the circumferential direction and having the shape on each of first and second ends;
the illumination window being formed partially in the circumferential direction to define third and fourth ends of the illumination window; and
the first and second ends of the mask overlapping the third and fourth ends of the illumination window to cover the third and fourth ends of the illumination window in the circumferential direction.

16. The endoscope according to claim 12, wherein the mask comprising a light blocking material applied partially to the light emitting surface of the illumination window, the light blocking material having an edge defining the shape.

17. The endoscope according to claim 12 further comprising a light blocking material disposed at least partially on a distal end face of the illumination window.

18. The endoscope according to claim 17, wherein the light blocking material is formed integrally with the mask.

19. The endoscope according to claim 12, further comprising a housing disposed proximally relative to the illumination window, the housing having a distal portion for holding the illumination window, the distal portion having one or more openings for guiding a light guide to a proximal end face of the illumination window.

20. An insertion portion for use with an endoscope, the insertion portion comprising:
a first projection projecting from a distal end of the insertion portion in a longitudinal axis direction, the first projection having an illumination window disposed on an outer peripheral surface of the first projection, the illumination window being disposed at least partially in a circumferential direction around the longitudinal axis direction so as to emit illumination light in the radial direction from a light emitting surface;
a second projection projecting from the distal end in the longitudinal axis direction at a position offset from the first projection in a radial direction; and
a mask configured to restrict emission of the illumination light in the radial direction from the illumination window, wherein the mask has a shape that increases in the radial direction from a proximal end side of the illumination window to a distal end side of the illumination window.

* * * * *